(12) United States Patent
Cuddihy et al.

(10) Patent No.: US 7,586,418 B2
(45) Date of Patent: Sep. 8, 2009

(54) MULTIFUNCTIONAL PERSONAL EMERGENCY RESPONSE SYSTEM

(75) Inventors: Paul Edward Cuddihy, Ballston Lake, NY (US); Jenny Marie Weisenberg, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 288 days.

(21) Appl. No.: 11/560,985

(22) Filed: Nov. 17, 2006

(65) Prior Publication Data

US 2008/0117060 A1 May 22, 2008

(51) Int. Cl.
*G08B 23/00* (2006.01)
*G04B 47/00* (2006.01)
(52) U.S. Cl. .................. 340/573.1; 368/10
(58) Field of Classification Search .......... 340/573.1, 340/309.15, 604, 605; 368/10
See application file for complete search history.

(56) References Cited

U.S. PATENT DOCUMENTS

| | | | | |
|---|---|---|---|---|
| 4,827,943 A | * | 5/1989 | Bornn et al. | 600/481 |
| 5,751,214 A | * | 5/1998 | Cowley et al. | 340/573.4 |
| 6,384,728 B1 | * | 5/2002 | Kanor et al. | 340/573.1 |
| 6,771,172 B1 | * | 8/2004 | Robinson et al. | 340/573.1 |
| 7,220,220 B2 | * | 5/2007 | Stubbs et al. | 482/72 |
| 7,292,135 B2 | * | 11/2007 | Bixler et al. | 340/286.07 |
| 2004/0152953 A1 | * | 8/2004 | Goedeke | 600/300 |

* cited by examiner

*Primary Examiner*—Benjamin C Lee
*Assistant Examiner*—Sigmund Tang
(74) *Attorney, Agent, or Firm*—Jenifer E. Haeckl (57) ABSTRACT

A system, for facilitating independent living of one or more individuals who has a health status and is located in a predetermined living area, that is adapted to communicate with one or more caregivers, that generally comprises: a first subsystem that monitors the activity levels of an individual and determines whether the activity level is indicative of a decline in said individual's health status; a second subsystem that can be selectively activated by the individual to alert caregivers that assistance is needed; a third subsystem that automatically alerts caregivers that assistance is needed based at least in part on determination of the first subsystem; and a fourth subsystem that monitors whether the individual is exhibiting wandering activity.

5 Claims, 9 Drawing Sheets

| Measure | Source | Description |
|---|---|---|
| Total Activity Count | actigraph | sum of all minute counts |
| Relative Amplitude (RA) | actigraph | strong activity and quiet sleep |
| Interdaily Stability (IS) | actigraph | consistency of activity rhythms across multiple days |
| Intradaily Variability (IV) | actigraph | brokenness of activity and rest in a single day |
| M10 | actigraph | activity count for most active 10 hours |
| L5 | actigraph | activity count for least active 5 hours |
| ALI | actigraph | number of minutes at moderate level of activity |
| Sedentary Time | actigraph, security, both | number of minutes sedentary |
| Sleep Duration | actigraph, security | length of sleep |
| Sleep Interruptions | actigraph, security | number of sleep interruptions |
| Sleep Interruption Time | actigraph, security | total time of sleep interruptions |
| Nighttime Bathroom Trips | actigraph, security | number of trips to the bathroom at night |
| 24-hour rhythm | actigraph | strength of 24-hour activity rhythm |
| Circadian Amplitude | actigraph | amplitude of fitted cosine curve |
| Circadian Mesor | actigraph | median of fitted cosine curve oscillation |
| Circadian Quotient | actigraph | ratio of circadian amplitude to circadian mesor |
| Circadian Acrophase | actigraph | time of day that peak activity occurs |
| Rhythm Percentage | actigraph | % of activity explained by fitted cosine curve |

FIG.6

*Healthier Patient*

Key Parameters:
- Amplitude
- Mesor
- Circadian quotient
- Rhythm percentage
- Acrophase

*Less Healthy Patient*

MULTIFUNCTIONAL PERSONAL EMERGENCY RESPONSE SYSTEM

BACKGROUND

Personal emergency response systems (PERS), that enable the user to alert emergency personnel that they are having a personal emergency or otherwise need assistance, are known and have been used by individuals for years. However, these devices have a narrow field of use and standard devices typically require the user to consciously trigger the alert system. More complex PERS devices utilize motion sensors in the home coupled with a pre-set number of hours to determine whether activity has occurred within that time period. Only in instances in which there has not been any activity within the pre-set time period is an alert triggered. Wandering, associated with dementia and Alzheimer's, has previously been monitored using motion sensors placed around the home or with a device, worn by the user, which transmits to a base station when pre-set limitations are breached. Although each of these devices offers a valuable benefit, it would be cost prohibitive and unwieldy to purchase and utilize all of the devices to monitor an individual's overall state of wellness.

BRIEF DESCRIPTION

Various embodiments of the personal wellness system described herein were developed to monitor the overall wellness of a user. One or more of the embodiments monitors the wellness of individuals using continuous activity data collected from monitoring devices that can be worn by the user without interfering in the user's daily activities such as a wristband or watch. This system uses real data collected from an individual as that individual goes about their normal daily activities to determine the individual's normal routine and to determine when, how and to what degree the individual's activities change or otherwise warrant additional consideration.

An embodiment of the system offers several long and short term health monitoring and alerting features, including, but not limited to: a wellness-monitoring and alerting system that monitors the long term health and wellness of an individual by monitoring a person's level of activity (e.g. high during the day and low during the night correlate generally with high physical function and good mental health) and reports accordingly to; a manually activated personal emergency response system (MPERS) that an individual can activate when he or she decides immediate assistance is needed; an automatically activated personal emergency response system (APERS) that can automatically alert caregivers of, a long term downward trend in an individual's health that requires the caregiver's particularized assessment, or a sudden decline in an individual's health (e.g. reflected by an abrupt decline in activity level); and a system that is adapted to determine whether an individual's time away from the home indicates a wandering event.

The total wellness and activity level features of such an embodiment are designed to help encourage use of the device even when the user feels healthy. When used to monitor overall health and wellness, the device no longer carries the stigma of a device that is used to call for help or that is specifically designed to monitoring wandering associated with diseases such as Alzheimer's. As such, it can be viewed as a device worn by healthy people who care about their health and desire to have an objective assessment of their overall health and wellness, rather than a device worn solely by elderly individuals that are too frail to get up if they fall.

An embodiment of the device is adapted to be worn on or proximate to the body with an accelerometer or other motion-detecting sensor. The device is capable of wired or wireless transmission of the data to a local or remote monitoring system.

This invention addresses multiple problems simultaneously. First, the personal emergency response system allows persons with a serious medical condition or the frail elderly to call for help as needed. This increases opportunity for independent living. Second, wellness and activity monitoring—exercise is an important aspect of health. It is important for all ages, but particularly for the aging and those dealing with medical conditions such as heart conditions to get regular exercise. Wearing a device that provides feedback on exercise by day and trends may increase exercise. The device is also adapted to detect whether an individual's sleep is good versus sleep that is interrupted. Third, automatic PERS—persons wearing a PERS device may need help but be unable to press the button due to a fall, or other physical or mental limitations. A device that learns normal patterns and can call automatically when there is unusual inactivity can assist the person in getting help within a few hours instead of days. Fourth, wandering or trouble indicated by the user being away from home too long, never leaving home, or leaving at an unusual time such as the middle of the night.

One or more of the embodiments of the system, for facilitating independent living of one or more individuals who has a health status and is located in a predetermined living area, that is adapted to communicate with one or more caregivers, generally comprises: a first subsystem that monitors one or more activities of the individual and determines whether changes in activity levels are indicative of a decline in the individual's health status; a second subsystem that is selectively activated by the individual to alert one or more of the caregivers that assistance is needed; a third subsystem that automatically alerts one or more of the caregivers that assistance is needed by the individual based at least in part on the determination of the first subsystem that activity levels have changed; and a fourth subsystem that monitors presence or absence from the individual's living area, and determines if the individual is exhibiting wandering activity based at least in part on one or more parameters such as time of day or duration of travel away from the living area. In some of the embodiments, at least a portion of each of the first subsystem, the second subsystem, the third subsystem and the fourth subsystem are housed within a single device that is adapted to be worn by the individual. The device is provided with a means for detecting whether the device is being worn or not. The device may be further configured to monitor one or more physiological indicators of the individual. The device may also comprise a means for remotely communicating directly with one or more of the caregivers, wherein the means for remotely communicating is preferably a wireless radio transmitter.

The first subsystem may be configured to determine whether the activity is indicative of a decline in the individual's health status in view of one or more predetermined health conditions associated with the individual. The first subsystem may also monitor one or more of the activities of the individual over various defined periods of extended time such as, but not limited to, greater than: one day, two days, one week, one month, two months, twelve months or two years, and stores data corresponding to the activities over the entire extended period of time, and automatically determines whether the stored data corresponding to the extended period of time is indicative of a decline in the individual's health status.

The first subsystem in some of the embodiments may comprise one or more sensors located within the predetermined living area and wherein the device is capable of engaging one or more of the sensors, wherein the device may comprise a data storage module for storing data corresponding to any engagement between one or more of the sensors and the device, and/or for otherwise storing data corresponding to the activities of the individual.

In some of the embodiments, the first subsystem, the second subsystem, the third subsystem and the fourth subsystem are all housed within a single device that is adapted to be worn by the individual.

In one or more of the embodiments, the system may comprise a base station, located proximate the living area, comprising a data storage module for storing data corresponding to the individual's activities; wherein at least a portion of each of the first subsystem, the second subsystem, the third subsystem and the fourth subsystem are housed within a single device adapted to be worn by the individual; and wherein the device comprises a transmitter for transmitting the data corresponding to the individual's activity level to the base station. Such embodiments may further comprise a plurality of sensors located in the living area that are adapted to detect one or more of the activities of the individual, wherein the worn device may comprise a receiver for receiving signals from the sensors that are indicative of one or more of the activities.

Some of the embodiments of the system, for facilitating independent living of one or more individuals who has a health status and is located in a predetermined living area, that is adapted to communicate with one or more caregivers, generally comprise: an device, comprising, a first subsystem that monitors one or more activity levels of the individual over an extended period of time and determines whether the activity is indicative of a decline in the individual's health status; a second subsystem that is selectively activated by the individual to alert one or more of the caregivers that assistance is needed; a third subsystem that automatically alerts one or more of the caregivers that assistance is needed by the individual based at least in part on the automatic determination of the first subsystem; and a fourth subsystem that monitors proximity to individual's predetermined living area, and automatically determines if the individual is exhibiting wandering activity based at least in part on time of day or duration of absence from living area; a means for transmitting information corresponding to the activities from the device to a location remote from the living area. The means for transmitting may comprise a base station in the living area, comprising a storage module for storing the information and a transmitter for transmitting the information from the living area to the remote location. The means for transmitting may further comprise a docking unit at the base station for docking the device to the base station for direct transmission of activity data from the device to the base station, and/or a radio transmitter in the device adapted to transmit activity data to the base station.

One or more embodiments of the system, for facilitating independent living of one or more individuals who has a health status and is located in a living area, that is adapted to communicate with one or more caregivers, generally comprise: an device, comprising, a first subsystem that monitors activity levels of the individual over an extended period of time; and a second subsystem that is selectively activated by the individual to alert one or more of the caregivers that assistance is needed; a base station comprising, a third subsystem that monitors whether an individual is away from the living area under unusual circumstances (e.g. based on duration away or time of day) that might indicate wandering activity away from the individual's living area; a fourth subsystem that automatically alerts one or more of the caregivers that assistance is needed by the individual based at least in part on the activities monitored by the first subsystem or the activities monitored by the third subsystem; a means for receiving data from the actigraphy device; and a base station transmitter for transmitting data from the base station to a location remote from the living area. The device may comprises a device transmitter for transmitting a signal, corresponding to the second subsystem alert, directly to one or more of the caregivers, wherein the means for receiving is wireless. Such embodiments may also comprise one or more sensors in the living area for sensing one or more of the activities of the individual, wherein the sensors comprise a signal transmitter for transmitting a signal to the device and/or to the base station when sensor is activated.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

An embodiment of the system comprises a plurality of functional features, including but not limited to: 1) wellness monitor—monitors activity level such as calorie burn per day, amount of exercise, total activity, quality of sleep, or other wellness or exercise measurements; 2) standard PERS—device has a push-button that calls for help like a standard Personal Emergency Response System; 3) automatic PERS—device learns normal activity levels and/or patterns and can automatically alert a third party when unusual changes in activity occur; and 4) wandering or unusual home/away activity—device knows when it is out of range of the base station. The fourth listed feature, for detecting wandering or unusual home/away activity, may be configured to alert health care or emergency care providers if the user leaves the home at an unusual hour or does not return on time, and/or configured to record when the user leaves and returns so that caregivers can ensure that the person is getting out and interacting with others.

An embodiment of the system may comprise a device that is worn on the body fitted with a panic button and an activity sensor, and one or more sensors that may also be worn or placed within the user's living area. The worn device transmits to a hub or base that is adapted to communicate to a remote location typically remote from the user's living area or home via telephone, the Internet, or any other appropriate communications link.

In addition to information or data transmitted from the user's living area to a remote location or terminal, the user may also receive incoming information and data, such as daily information on exercise and activity levels, via the device directly, the hub or base, a home PC, TV or other video or telephonic device within the living area or home. Such feedback and information enables the user to be involved with their own health decisions and activity schedule and to understand and track trends in their own activity against preset goals.

The device also has panic button features. The system is also capable of computing normal activity levels and patterns. This computation takes place either on the hub or at a central processing facility that receives activity readings from the home on a periodic basis.

An alert can be generated if the device is being worn but activity levels are unusual. For example, the individual may be up all night, or there is an abrupt lack of activity indicating fall, or very low activity as might be expected with a flu. The alert goes to a third party such as family caregivers or a standard PERS monitoring center. Alerts may also be generated if the device is not worn for a certain amount of time. For persons who normally take the device off at night, an alert may be generated if they fail to put it back on in the morning. Other types of abnormal activity or abnormal removal patterns may generate alerts. The system also knows when the device is out of range of the base station. This indicates the user is away. This information can be used to trigger alerts for wandering, late return time, or leaving at an unusual time such as the middle of the night.

All data on activity levels and home/away could potentially be provided to formal or informal caregivers who want to assess the quality of lifestyle of the user. The user should have complete control as to who can see the data.

It is desirable that the device transmits data without user interaction, and that the interface is extremely simple. The device should have a long battery life and require very low maintenance.

Further, PERS functions may not operate when the device is out of range of the base station, but the device will nonetheless store activity data and transmit it once it is back in range of the base station. The device also comprises a sensor to determine when the device is not being worn to prevent false alarms and to possibly notify the caregiver if the person is unprotected.

Figure 1:
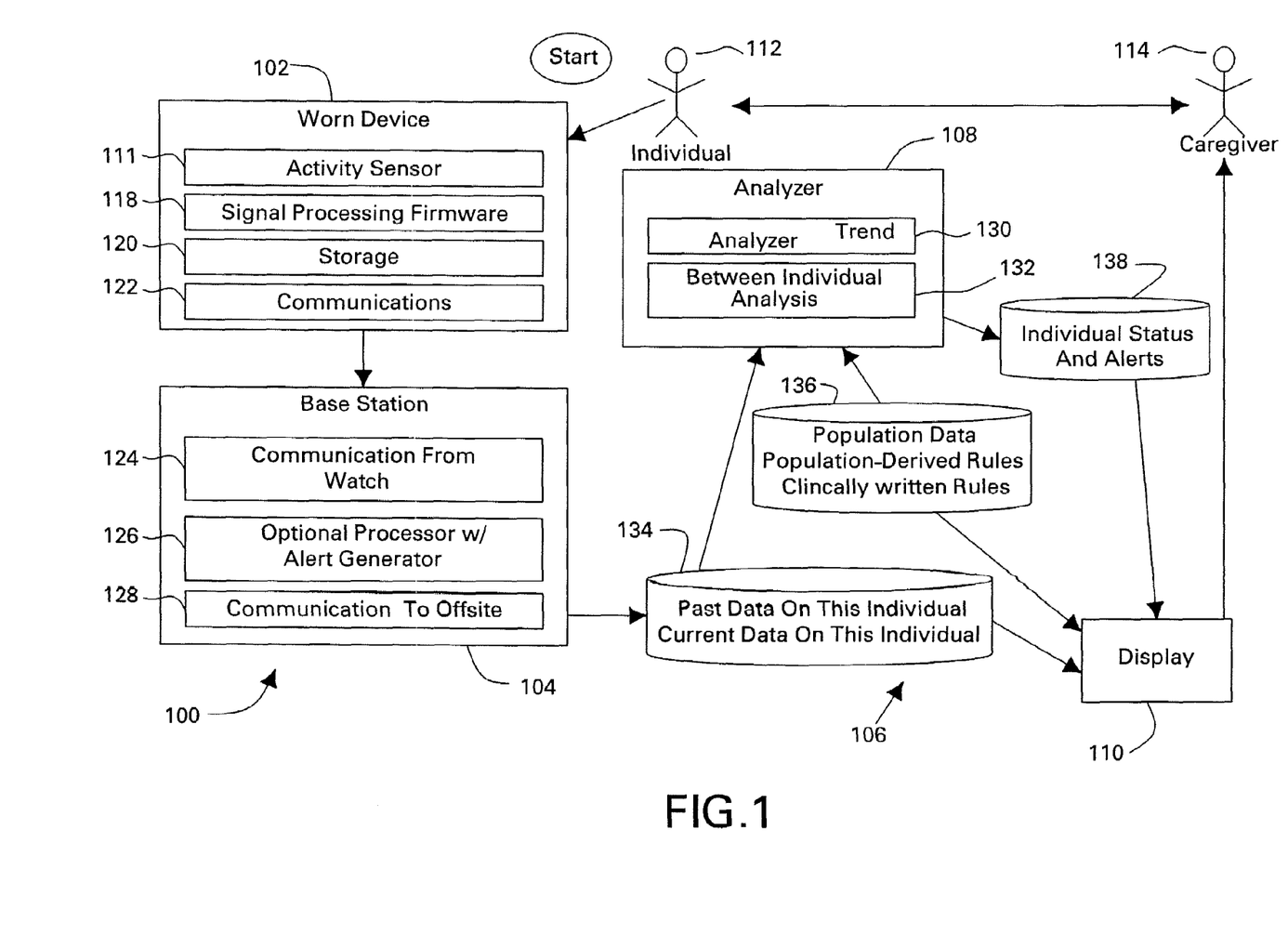
FIG. 1 is a flow diagram of an embodiment of the system of the invention for monitoring and reporting the long term and short term health and activity of an individual, and alerting caregivers when necessary.

An embodiment of the system is shown and generally referred to in FIG. 1 as system 100. System 100 comprises one or more personal devices 102, one or more hubs or base stations 104, one or more local or remote databases 106, and one or more local or remote processors 108. Such remote databases or processors may reside in or otherwise communicate with monitoring center 440. Monitoring center 440 may be configured to be accessible by the individual or authorized caregivers through the Internet or any other suitable wired or wireless means. Device 102 preferably comprises a display 110. Device 102 is preferably a user-wearable, non-encumbering device. Device 102 comprises an activity and/or a movement sensor 111 that substantially, continuously monitors and collects the daily-activity data of user 112. Processor 108 may be embodied within device 102, base station 104 and/or a remotely located processing system. The data collected by device 102 may be directly analyzed by processor 108 if housed within device 102 or the data may be transmitted to base station 104 or a remote processor. The data may be transmitted wirelessly or by hardwire System 100 may also comprise one or more sensors in addition to the sensor embodied within device 102. A plurality of sensors may be positioned throughout the living area to monitor the individual's more specific activities.

If the processor in the device, base station, or remote monitoring center makes a determination from the daily-activity data of individual 112 that a change in of the activity level of individual 112 has occurred, the processor generates an indication of the change for access by a remote caregiver 114. If desired, system 100 may be configured to send an alert to a caregiver 114 only upon a determination from the daily-activity data of individual 112 that individual 112 needs medical review or assistance. For example, an alert may be generated only upon a determination from the daily-activity data of the individual 112 that a substantial change in activity level is taking, or has taken, place that may require immediate assistance or careful medical review. For example, medical review may occur within two to three days of receipt of the indication of the change in condition for non-emergency medical attention. The remote caregiver 114 may be presented trends over hours, days and/or weeks to verify treatment effectiveness or stabilization of condition of individual 112. If the data indicates an immediate problem, then an alert may be generated, either to the individual's personal caregiver 114 or directly to emergency personnel such as a local EMT or ambulance service.

Device 102 allows individual 112 to move about the living area unencumbered while device 102 unobtrusively, automatically and virtually, continuously monitors and collects daily-activity data associated with individual 112. As noted, device 102 may be configured to house a movement sensor 111 and one or more of signal processing firmware 118, storage 120, transmitter 122, a sensor to determine whether the device is being worn or not worn, and/or processor 108. The sensor to determine whether the device is being worn may comprise a temperature sensor and/or magnetic, electrical or light based contact/circuit sensors. Device 102 may be configured to monitor movement, acceleration, vibration, and/or change in orientation. For example, device 102 may comprise one or more of an accelerometer, actigraph, pendulum-based pedometer tilt switch, vibration sensor, location sensor (e.g. calculates distance traveled), and/or motion detector.

Device 102 is preferably capable of measuring activity levels over twenty-four hour periods for a relatively long-term duration. If desired, device 102 may be configured to measure one or more physiological parameters of individual 112, such as temperature, blood pressure, heart rate and blood sugar, as well.

Device 102 may be housed or otherwise embodied in any convenient, but comfortable, wearable accessory such as, but not limited to, wristbands (FIG. 3), wrist or pocket watches, necklaces, pendants and bracelets. Device 102 preferably comprises a data collection means that comprises signal processing firmware 118 and/or storage device 120.

Figure 3:
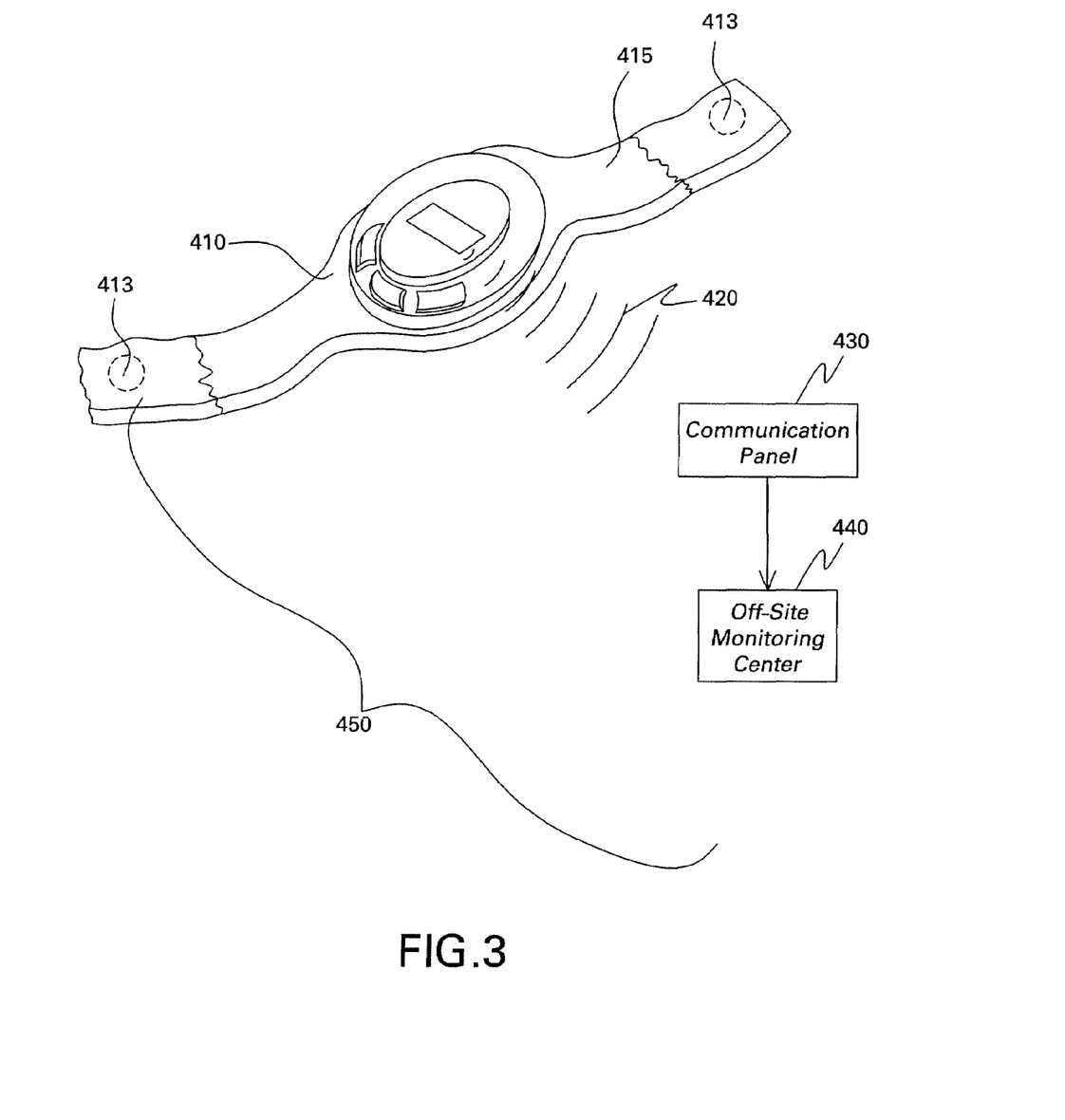
FIG. 3 is a perspective view of an embodiment of the independent activity detector system of the invention.

As shown in FIG. 3, an embodiment of the independent activity detector system 450 includes an independent activity level detector 410, a communication panel or base station 430 and an off-site monitoring center 440. The independent activity level detector 410, which is configured to be worn by a person for whom activity data is to be determined, is enabled to measure one or more of movement, acceleration, vibration, and change in orientation. Although the activity level detector is illustrated as a watch in FIG. 3, the activity level detector may take any number and types of forms that are wearable on a person or a person's clothing. For example, the independent activity level detector 410 may be equipped with a chain or other such apparatus for hanging the detector 410 from one's neck as a pendant or with a clip or pin to attach to clothing. Independent activity level detector 410, as illustrated, may comprise a strap 415 for attaching to a person's wrist or ankle. The sensors 413, for determining whether the device is being worn, may be located on the ends of the wristbands and positioned so that they are in contact when the device is worn. Alternatively, the sensor may be positioned on the backside (not shown) of the device, e.g. to measure temperature. The independent activity detector 410 may be incorporated within a timepiece, such as a watch. It should be appreciated that the independent activity level detector 410 may be equipped with other means of wearing the device instead of the strap 415, such as, for example, a hook, clip, pin, etc. so that the device may be worn on a person's belt or clothing. It should be appreciated that any mechanism for associating the independent activity detector 410 to one particular person is within the scope of the invention, including adhesives, mechanical attachment devices, embedding within the person's clothing, or other suitable mechanism.

Figure 4:
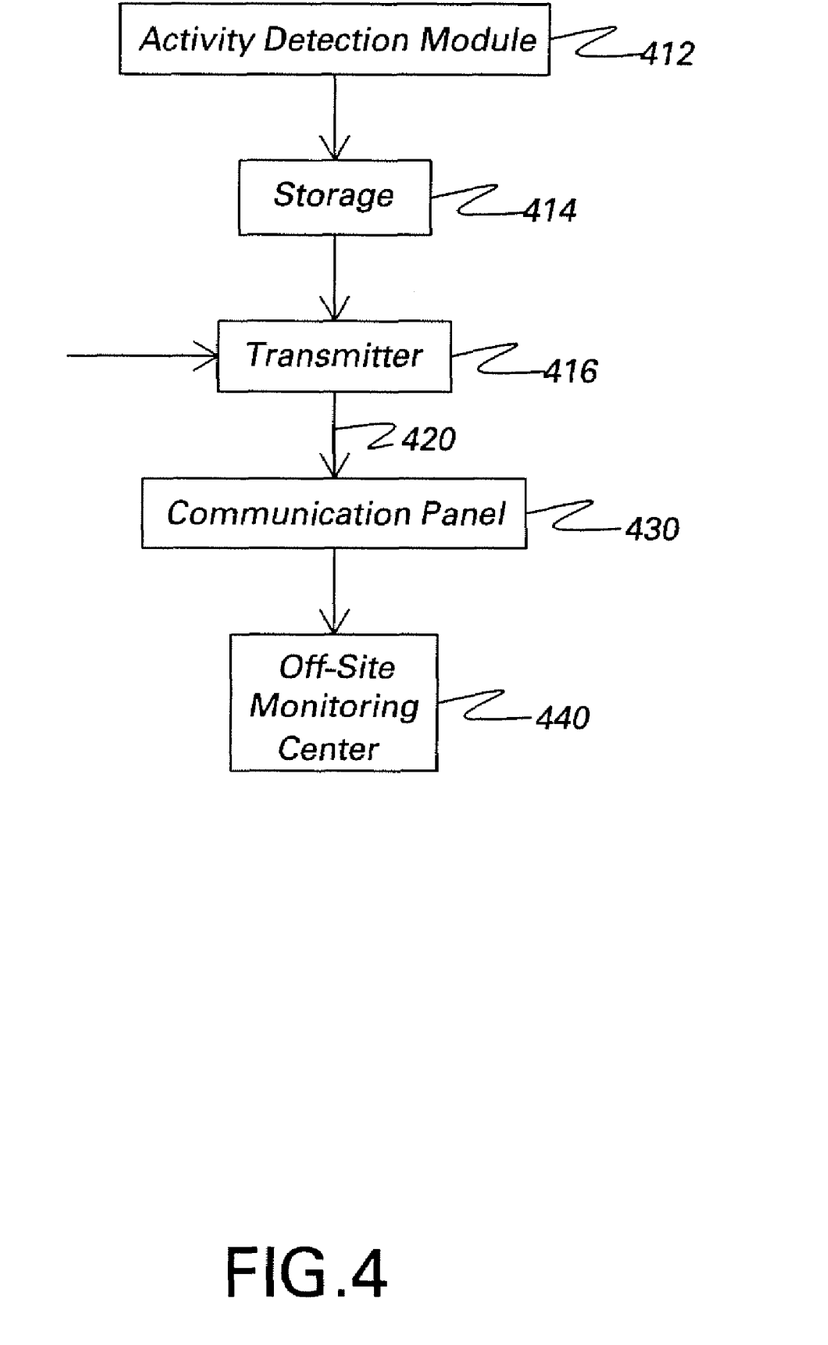
FIG. 4 is a flow diagram of an embodiment of the system for monitoring activity levels.

As shown in FIG. 4, the independent activity level detector 410 may comprise activity detection module 412, storage means 414, and transmitter 416, and, as noted, a means to detect whether it is being worn. The activity detection module 412, which is configured to detect the activity of the person wearing the independent activity level detector 410, may be any suitable such apparatus. Storage means 414 may be configured to store all the data collected by the activity detection module 412 until such time that the data is transmitted from the independent activity detector 410. Further, storage device 414 may be configured to retain packets of data for a period of time after transmission of such data. Storage means 414 may be any suitable memory device, such as, for example, a RAM memory chip.

Transmitter 416 is configured to wirelessly transmit data from the independent activity level detector 410 to a receiver. Detector 410 may also include a receiver (not shown) for receiving an acknowledgement of its transmission or other information. Having such a receiver on detector 410 enables detector 410 to transmit only the necessary data.

The receiver for the transmission from the transmitter 416 is a communication relay, such as the communication panel 430. The communication relay may be a wireless hub. Transmission of data may be continuous or may be accomplished using a series of data packets sent in the transmission.

A personal emergency response system (PERS) 418 is preferably provided in one or more embodiments of the system of the invention and may be included at part of independent activity detector 410. A person who has fallen and may be injured, but is still conscious and capable of activating PERS 418, may activate PERS 418. A means for activating the PERS 418 may comprise, but is not limited to, a button, pad or switch provided on, or within, detector 410 to enable the individual to activate an alert. Regardless whether PERS 418 is manually or automatically activated upon a fall, or upon detection and analysis of any unusual activity or inactivity, the independent activity detector system 450 can detect unusual activity or inactivity on a real or quasi-real time basis. Utilizing an activity detection module 412, such as an accelerometer, a mercury switch, or other suitable activity-detecting apparatus, the independent activity detector 410 collects data pertaining to the activity or inactivity and either stores such data in a storage module 414 and further processes the data within detector 410, or transmits the data to the base station 104 or to a remote monitoring center 440.

Figure 2:
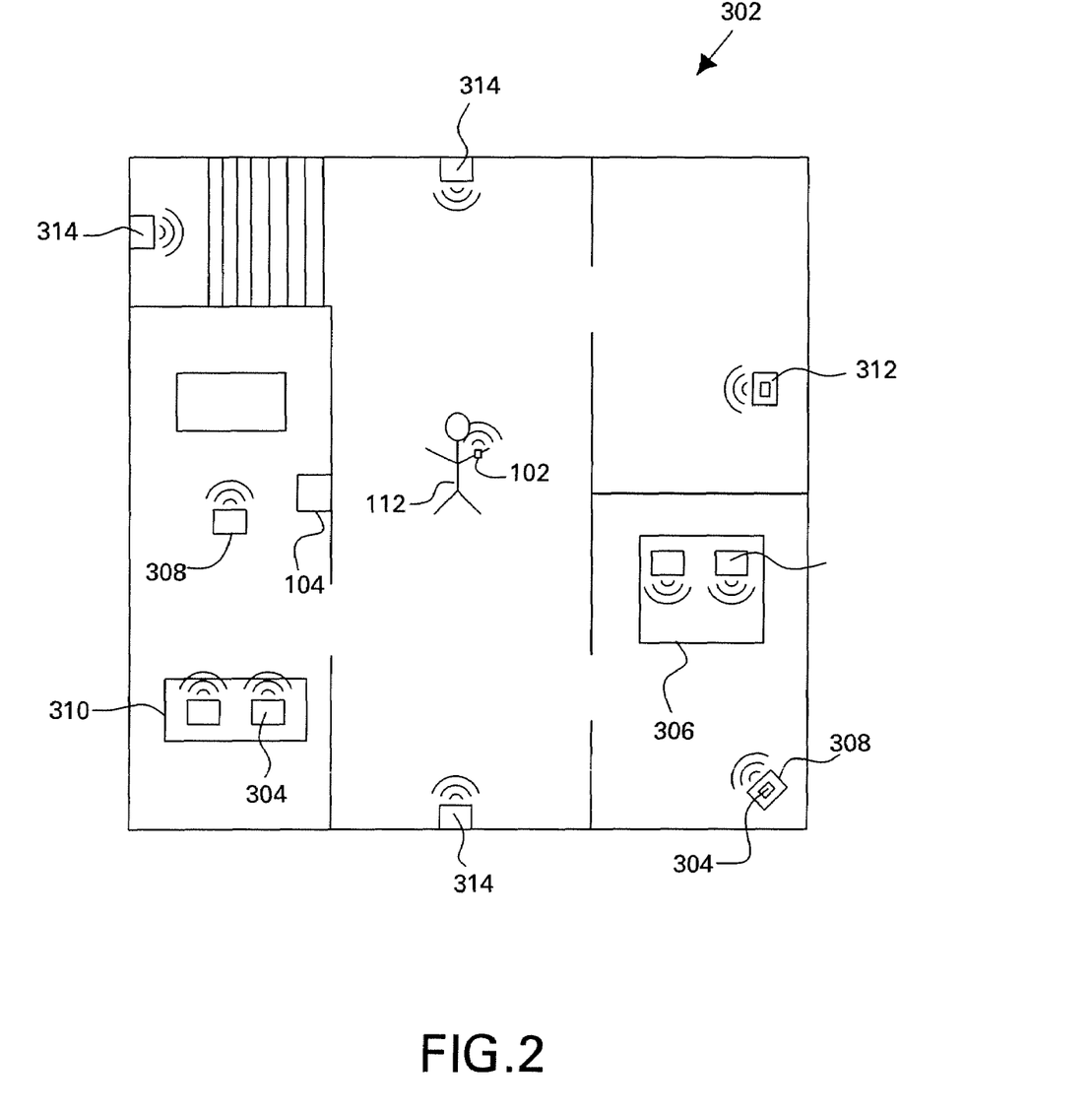
FIG. 2 is a diagrammatic view of a portion of an embodiment of an in-home system of the invention in use within a living area.

With reference to FIGS. 1 and 2, the daily-activity data of individual 112 is collected for immediate, periodic, activated, or delayed transmission, by the transmitter 122. For example, in an embodiment in which the data processing does not occur within device 102 but rather at base station 104 and/or at monitoring center 218 or 440, the data may be stored, for later transmission, when the collector of the device 102 is out of range of the base station 104. Transmitter 122 may be configured to continuously, automatically at set time intervals and/or when requested to send the daily-activity data of the individual 112 to the base station 104. The transmitter 122 preferably comprises a radio transmitter that transmits the daily-activity data of the individual 112 to the base station 104. However, other suitable means of transmission may be used. For example, transmitter 122 may be configured to dock with base station 104 to transmit the daily-activity data.

Once base station 104 receives the daily-activity data of the individual 112 from the transmitter 122, the daily-activity data may then be processed and analyzed by processor 108. The processing may be continuous or periodic depending on the configuration desired. Base station 104 may also comprise one or more receivers 124, an alert generator 126, and/or a transmitter 128. As noted, device 102 may alternatively, or in addition, include a manual and automatic alert generator. Base station 104 in one example comprises processor 108. Depending on the amount of data collected and whether the database resides in device 102, base station 104 or a remote monitoring center, databases 106 may comprise one or more of a past and current individual data database 134, a population data and rules database 136, and/or a individual status and alert database 138. One or more of the past and current individual data database 134, the population data and rules database 136, and/or the individual status and alert database 138 may be combined in a single database.

The past and current individual database 134 may store the activity data, past and present, for individual 112 along with results of analysis. The population data and rules database 136 stores population models that assign logic to activity values, shifts, and/or trends of the individual 112. This logic may be derived empirically from studying other individuals and/or outcomes. The system may also utilize rules based on clinical knowledge. The individual status and alert database 138 holds trends and alerts that potentially need to be reviewed by the remote caregivers 114. Processor 108 may be configured to perform a baseline versus substantially continuous comparison of movement and/or activity data on the individual from home as an indirect measure of health of the individual. Processor 108 employs the daily-activity data of the individual 112 to estimate the probability of future events related to the health of the individual.

Based on the logic provided, the system may be configured to automatically identify changes in the activity data of the individual and to identify activity trends. Such trends can be based on the individual's own data collected and analyzed over short or long periods of time and/or on data collected from, or representing, a group or population of other individuals. For example, the activity data can be classified as normal or abnormal to determine whether further personalized diagnosis and intervention is required by a health care professional as the remote caregiver 114 or emergency medical personnel.

The system may comprise an individual processor 130 and/or a individual group processor 132. For example, processor 108 makes a determination from the daily-activity data of individual 112 that the change in condition of individual has occurred. Processor 108 generates the indication of the change in condition of individual 112 for access by the remote caregiver. Processor 108 generates the alert to the remote caregiver only upon a determination from the daily-activity data that the individual needs a more personalized medical review or immediate emergency assistance.

One or more embodiments of the system combine long-term analysis associated with disease progression or a relatively slow decline in health with short term, acute situations that require immediate emergency response. For example, the system may be configured to monitor and review, over a relatively long period of time, the circadian rhythms of patients with dementia or the levels of activities of patients known to have congestive heart failure. The system can remove from health assessment subjective observations made by the individual and the individual's family or day-to-day caregivers who may not be as aware of such long-term changes. If an individual begins to slow down, sleeps for longer periods of time, or tires easily, the system 100 automatically monitors and collects such data, quantifies and analyzes the data, and if necessary, alerts a health care professional that the individual is in decline or, if the individual's symptoms are acute, alerts an emergency medical team. The system can also be used to monitor and verify improvement after treatment or assistance, and whether any such improvement is maintained. One benefit of the system is the ability to send wellness data to the individual, such as exercise levels, to help motivate the individual to remain active and to cast a positive healthy light on the use of this device.

With reference to FIG. 2, individual 112 is shown located in a home or living area 302. As previously described, device 102 may be employed alone or with other personal devices and/or with other sensors placed around the living area of the individual. For example, pressure pads and/or sensors 304 are located in a bed 306, chairs 308, a sofa 310, and/or a scale 312 of the individual 112. As shown in the embodiment illustrated in FIG. 2, motions sensors 314 are located in the rooms, hallways, doorways, and/or stairways of the home 302. Pressure sensors or load cells 304, e.g. bed/chair occupancy sensors such as pressure pads, and motions sensors 314 may be configured to communicate with device 102 and/or with base station 104 depending on the location of the data processors.

Figure 5:
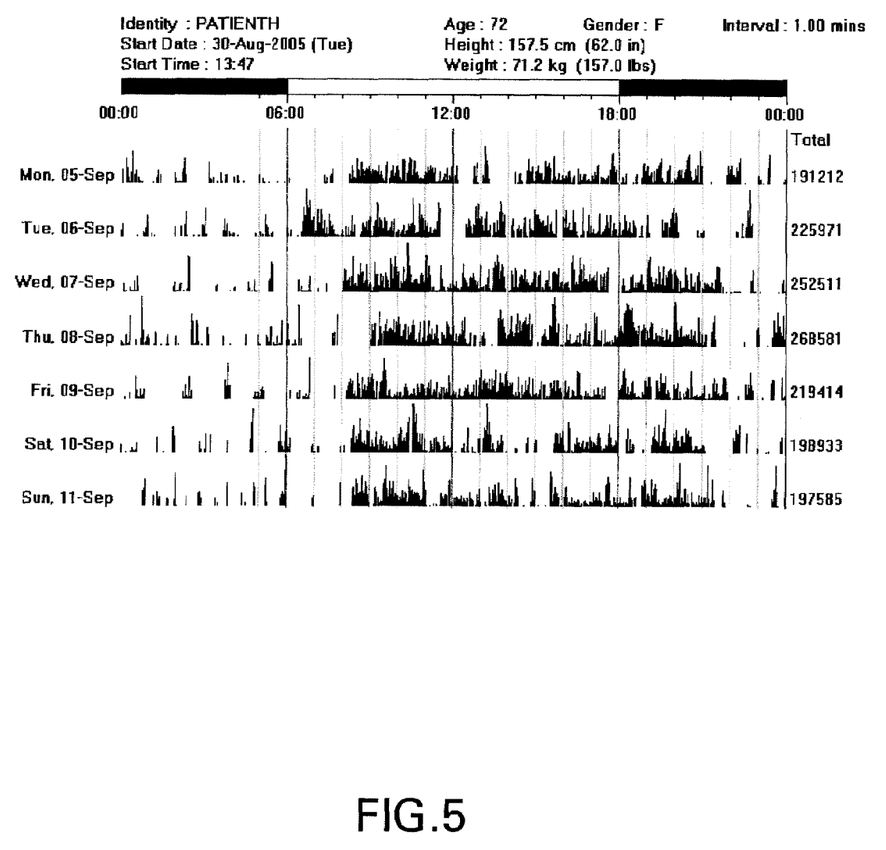
FIG. 5 is a graph of an example of the type raw activity data collected and analyzed by one or more embodiments of the system.

The data collected by device 102 and any of the other types of sensors employed with the embodiments of the system is collected as raw activity data such as the data shown in FIG. 5. FIG. 5 is a graph of raw activity data collected over a relatively short period of time, using an actigraphy watch, from midnight on a Monday, September 5$^{th}$ through just before midnight seven days later on Sunday, September 11$^{th}$. In this embodiment, the data is collected and stored in 1-minute epochs or intervals, however, the epoch may be any value. The data shown has been compressed to illustrate the data in a graph format. As the graph shows, this individual generally begins sleep between 9:00 and 11:00 pm and sleeps until about 8:00 am. However, the graphed data readily shows that this individual apparently awoke about and hour and a half earlier than usual on Tuesday but went to bed that evening an hour earlier than usual as well. The activity count, which is a representation of the person's activity level, is shown on the right side of the graph. On its face, this data indicates that the individual was considerably more active over the course of the day, at least within the area detected, on Thursday than on Monday. The graph indicates that the person's activity count was 268,581 on Thursday but only 191,212 on Monday. In general, the individual was considerably more active on Tuesday through Friday than on Saturday through Monday. The information from this data may be further assessed based on additional information specific to the individual, empirical data from other sources, as well as activity data from other sensors in various locations in the individual's living area.

Figure 6:
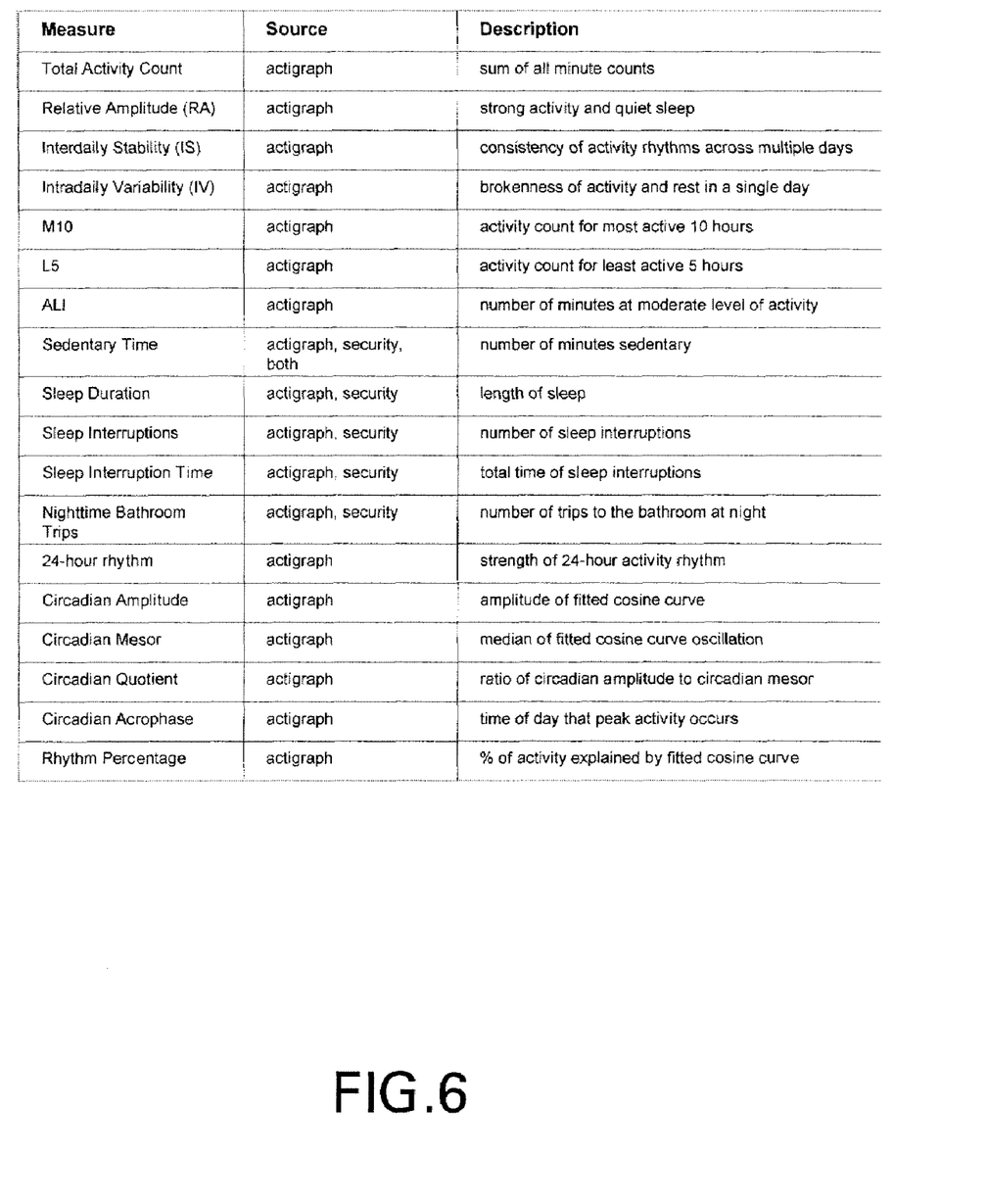
FIG. 6 is a table of examples of activity metrics that may be calculated by the system from the raw activity data collected by the monitoring device of the system.

When using a motion sensor to collect activity data, various metrics may be used to assess these activities. Some of these metrics are listed and described in FIG. 6. This list of metrics is illustrative rather than exhaustive and other useful metrics may be calculated from the raw activity data. As noted, means other than actigraphy watches and motion detectors may also be used to monitor and collect activity data, as well as physiological data if desired for a given individual or situation. These metrics are calculated or processed from the raw activity data and used to analyze the activity status of the individual.

Figure 7:
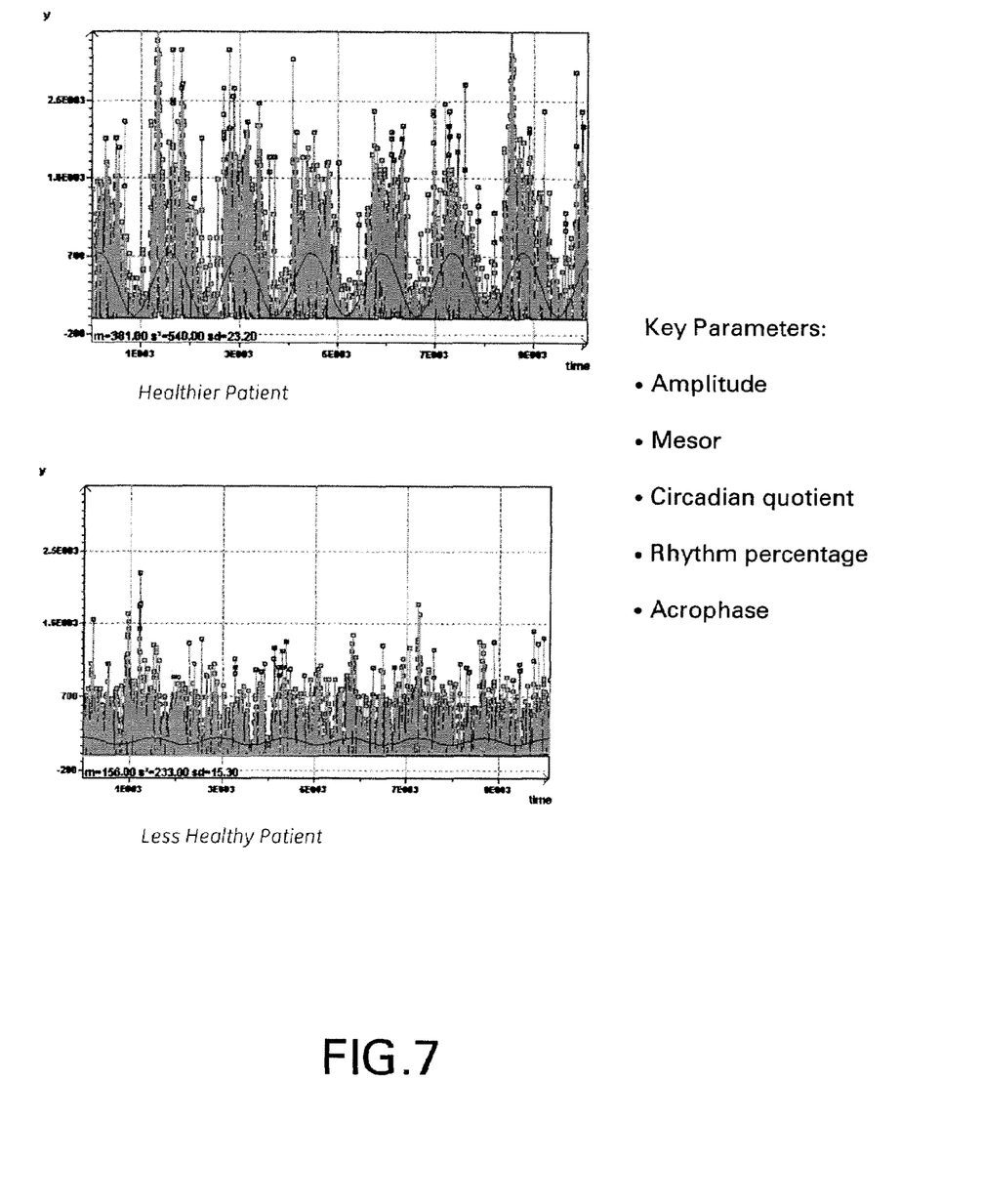
FIG. 7 comprises two graphs of activity data for comparison of activity of a healthier patient with the activity of a less healthy patient with a legend of parameter examples that may be used by the system of the invention to analyze activity data.

As shown in FIG. 7, various analytical tools may be utilized to analyze the data depending on a given individual's health concerns. In FIG. 7, a cosinor analysis of the collected activity data over a week period of time is illustrated with two comparative graphs of a healthier individual and a less healthy patient. Key parameters that may be used in these types of analytical tools include but are not limited to amplitude, mesor, circadian quotient, rhythm percentage and acrophase. As is quite apparent from a comparison of the two graphs shown in FIG. 7, the less healthy individual is considerably less active than the healthier individual. The healthier individual also has clear patterns of activity and inactivity typically associated with active daily routines and consistent sleep habits. The system is adapted to determine whether an individual's sleep is healthy uninterrupted sleep or sleep that is interrupted and inconsistent.

The system may also be configured to collect and analyze long term activity to monitor an individual for declines and changes in activity that are subtle or occur over an extended period of time. Long-term data is particularly useful when monitoring individuals with chronic illnesses such as congestive heart failure. Two examples of long term monitoring results are shown in FIGS. 8 and 9.

Figure 8:
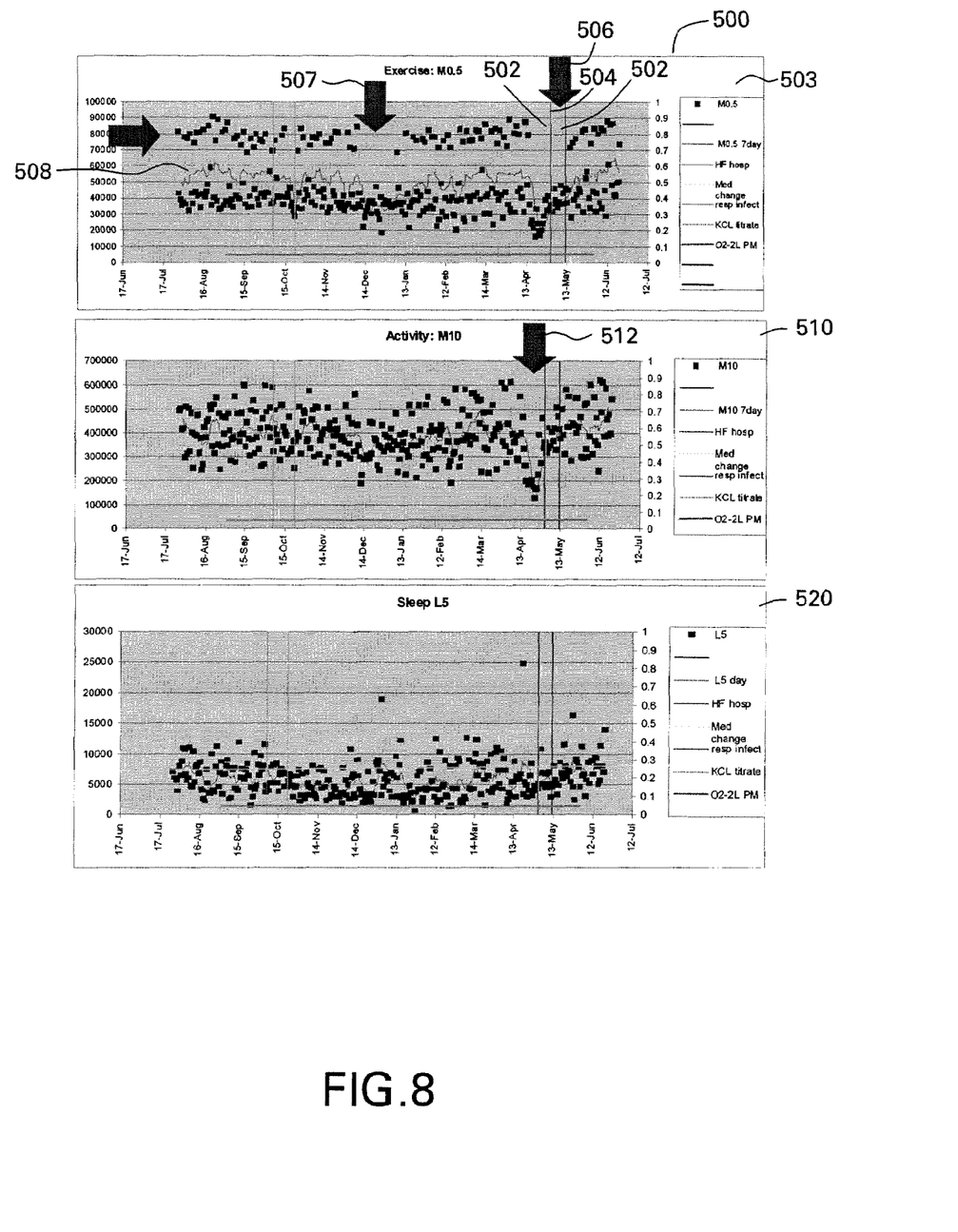
FIG. 8 comprises three graphs that together show an example of long-term activity data for a relatively healthy patient that is graphed according to three example categories of activity, exercise, general activity, and sleep.

FIG. 8 shows the activity levels for an individual monitored over about 13 months using an embodiment of the system. The activity levels are illustrated in this example using three graphs of compressed activity data for exercise 500, activity 510 and sleep 520. Graph 500 shows the individual's exercise activity of the 13-month period of time. Legend 502 is provided to designate information specific to the individual that aid in the analysis of the activity data. The bold arrows indicate areas of activity that should be further reviewed. This individual is a relatively healthy individual that is suffering over time from congestive heart failure. The graphed data shows that the individual's activity is quite stable over the 13-month period of time except for a break in exercise in December and a sharp decline in exercise and overall activity (arrow 512) in late April into early May. The break in exercise may have been due to the individual's busy holiday schedule, which prevented the individual from exercising. The decline in exercise and activity beginning in April is indicative of an ensuing respiratory infection. The period of infection 504 is illustrated using lines 502 and arrow 506. Line 508, shown in each of the three graphs, shows a running average of the activity levels over the 13-month time period. As these graphs show, coupling such long-term activity data with medical and personal information about a given individual enables negative health events to be detected. In the embodiment illustrated in FIGS. 8 and 9, M0.5 represents activity during the busiest ½ hour of the day.

Figure 9:
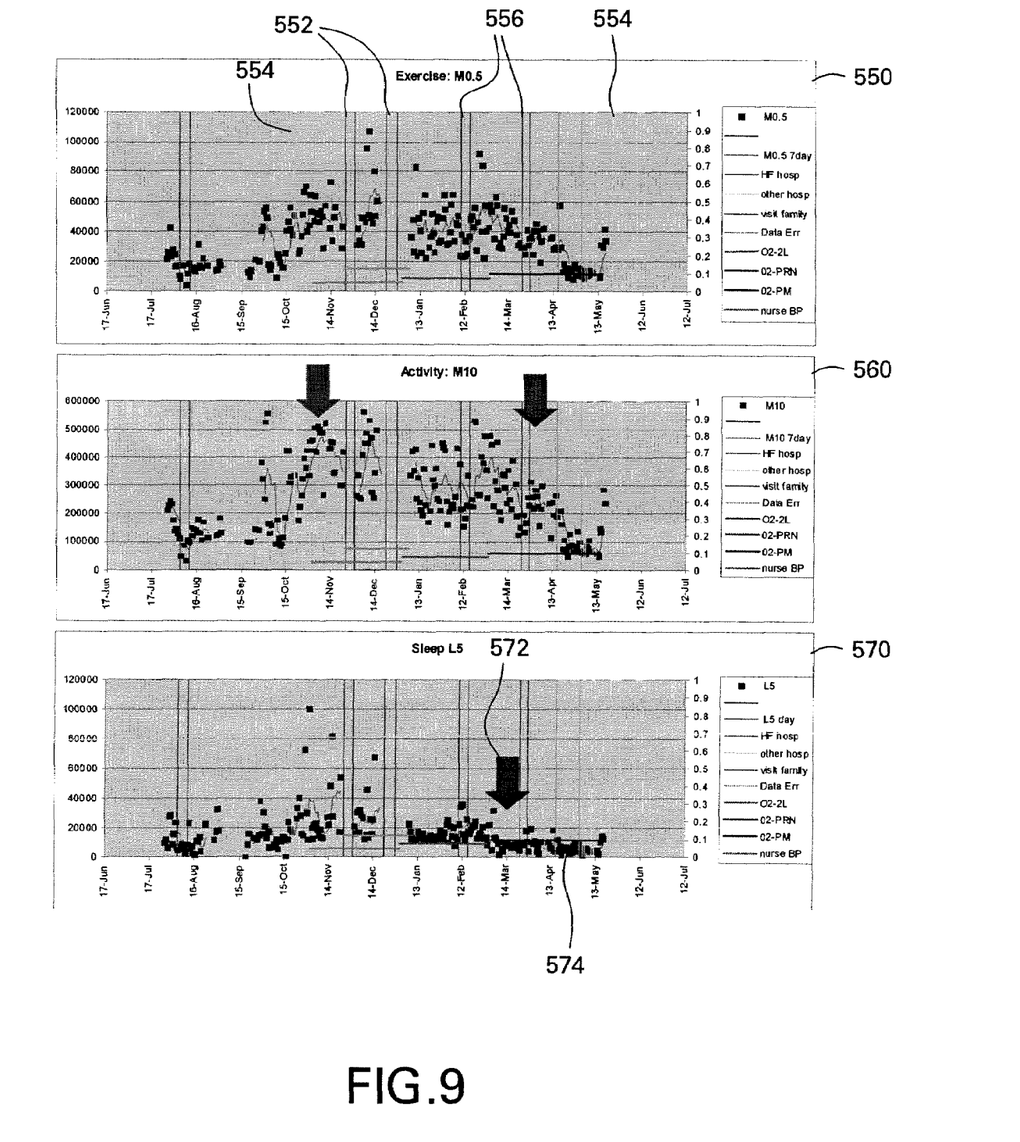
FIG. 9 comprises three graphs that together show an example of long-term activity data for less healthy patient that is graphed according to three example categories of activity, exercise, general activity, and sleep.

FIG. 9 shows the monitored activity levels for another individual over a 13-month period of time. The activity levels are similarly illustrated in this example using three graphs of compressed activity data for exercise 550, activity 560 and sleep 570. The activity data is shows activity levels that are inconsistent and have significant gaps. Identifiable gaps 552 in the data correspond with family visits away from the monitoring area. This individual also had multiple hospitalizations over the 13-month period of time. Lines 556 indicate hospitalizations related to heart failure and lines 554 indicate a hospitalization for shoulder surgery in October and for other problems in May and June. The data is less stable over time, which is indicative, in this case, of the individual's relatively unhealthy status. Graph 570 of the individual's sleep activity shows that the individual often has difficulty sleeping from about August through about February. However, the individual's sleep greatly improves beginning in the middle of March, as shown by arrow 572, when an evening oxygen regimen is initiated as shown by line 574. Such data serves as an objective, confirmation that medical intervention, such as administration of oxygen, is achieving a beneficial result.

As these examples illustrate, the system effectively monitors and provides direct and indirect measures of health indicators such as sleep quality and caloric expenditure. Exercise, sleep and overall activity are three illustrative, but not exhaustive, measurable types of indicators that can be used to indirectly indicate health problems, or symptoms of health problems, such as, but not limited to, chest pain, coughing, difficulty breathing, shortness-of-breath, fatigue, or swollen legs, anyone of which may affect the level and extent of exercise, sleep or overall activity. As noted, a variety of sensors may be employed throughout a living area to measure specific and general activities such as pressure sensors 304 which may be sued to monitor sleep quality, sleep location, and/or information related to more sedentary activities. Motion sensors 314, for example, are useful for monitoring activity that requires individuals to move themselves or to move an object.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system, for facilitating independent living of one or more individuals who has a health status and is located in a living area, that is adapted to communicate with one or more caregivers, comprising:
   a monitoring device, comprising,
      a first subsystem that monitors one or more of activity levels of said individual over an extended period of time; and
      a second subsystem that is selectively activated by said individual to alert one or more of said caregivers that assistance is needed;
   a base station comprising,
      a third subsystem that monitors whether said individual is exhibiting wandering activity away from said individual's living area;
      a fourth subsystem that automatically alerts one or more of said caregivers that assistance is needed by said individual based at least in part on changes in activity levels as determined by said first subsystem or said third subsystem;
      a means for receiving data from said monitoring device; and
      a base station transmitter for transmitting data from said base station to a location remote from said living area.

2. The system of claim 1, wherein said actigraphy device comprises a device transmitter for transmitting a signal, corresponding to said second subsystem alert, directly to one or more of said caregivers.

3. The system of claim 1, wherein said means for receiving is wireless.

4. The system of claim 1, further comprising one or more sensors in said living area for sensing one or more of said activities of said individual, wherein said sensors comprise a signal transmitter for transmitting a signal to said actigraphy device when said sensor is activated.

5. The system of claim 1, further comprising one or more sensors in said living area for sensing one or more of said activities of said individual, wherein said sensors comprise a signal transmitter for transmitting a signal to said base station when said sensor is activated.

* * * * *

UNITED STATES PATENT AND TRADEMARK OFFICE
CERTIFICATE OF CORRECTION

| | | |
|---|---|---|
| PATENT NO. | : 7,586,418 B2 | Page 1 of 1 |
| APPLICATION NO. | : 11/560985 | |
| DATED | : September 8, 2009 | |
| INVENTOR(S) | : Cuddihy et al. | |

It is certified that error appears in the above-identified patent and that said Letters Patent is hereby corrected as shown below:

On the Title page, in the Figure, for Tag "136", Line 3, delete "Clincally" and insert -- Clinically --, therefor.

In Fig. 1, Sheet 1 of 9, for Tag "136", Line 3, delete "Clincally" and insert -- Clinically --, therefor.

In Fig. 5, Sheet 5 of 9, delete "PATIENTH" and insert -- PATIENT --, therefor.

Signed and Sealed this

Twenty-third Day of November, 2010

David J. Kappos
*Director of the United States Patent and Trademark Office*